(12) United States Patent
Hanai et al.

(10) Patent No.: US 6,188,025 B1
(45) Date of Patent: *Feb. 13, 2001

(54) HEAT-RESISTING METAL-SHEATHED CABLE FOR SENSOR

(75) Inventors: Shuichi Hanai, Nagoya; Takashi Nakao, Aichi; Hisaharu Nishio, Aichi; Katsuhisa Yabuta, Aichi, all of (JP)

(73) Assignee: NGK Spark Plug Co., Ltd., Nagoya (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/972,734

(22) Filed: Nov. 18, 1997

(30) Foreign Application Priority Data

Nov. 18, 1996 (JP) .................................... 8-306490

(51) Int. Cl.$^7$ ..................................................... H01B 7/18
(52) U.S. Cl. .................................. 174/102 R; 174/102 P
(58) Field of Search ............................ 174/102 R, 102 C, 174/102 P, 96

(56) References Cited

U.S. PATENT DOCUMENTS

| | | | |
|---|---|---|---|
| 4,269,639 | * | 5/1981 | Lewis ............................ 156/54 |
| 4,439,255 | * | 3/1984 | Imai et al. ..................... 156/49 |
| 4,679,317 | * | 7/1987 | Bailleul et al. ................ 29/828 |
| 5,111,002 | * | 5/1992 | Hollander ..................... 174/102 R |
| 5,271,821 | * | 12/1993 | Ogasawara et al. ........... 204/429 |
| 5,464,485 | * | 11/1995 | Hall, Jr. ........................ 136/230 |
| 5,928,494 | * | 7/1999 | Kato et al. .................... 205/781 |
| 5,948,225 | * | 9/1999 | Katafuchi et al. ............. 204/421 |
| 5,999,081 | * | 12/1999 | Hannigan et al. ............. 338/28 |

FOREIGN PATENT DOCUMENTS

| | | |
|---|---|---|
| 40 07 553 | 9/1991 | (DE) . |
| 19523911 | 1/1997 | (DE) . |
| 0 145 060 | 6/1985 | (EP) . |
| 2 143 162 | 2/1985 | (GB) . |
| 56-4852 | 6/1955 | (JP) . |
| 8-201338 | 8/1996 | (JP) . |
| 8-219902 | 8/1996 | (JP) . |
| 10-505428 | 5/1998 | (JP) . |

\* cited by examiner

*Primary Examiner*—Kristine Kincaid
*Assistant Examiner*—William H Mayo, III
(74) *Attorney, Agent, or Firm*—Foley & Lardner

(57) ABSTRACT

A heat-resisting metal-sheathed cable for a sensor includes: an outer sheathing tube made of a heat-resisting metal; an inner sheathing tube made of a heat-resisting metal and disposed within the outer sheathing tube with a predetermined gap that includes an open ventilation passage between an inner circumferential surface of the outer sheathing tube and an outer circumferential surface of the inner sheathing tube; at least one conductor disposed within the inner sheathing tube; and a mass of insulating powder disposed within the inner sheathing tube and around the at least one conductor.

4 Claims, 6 Drawing Sheets

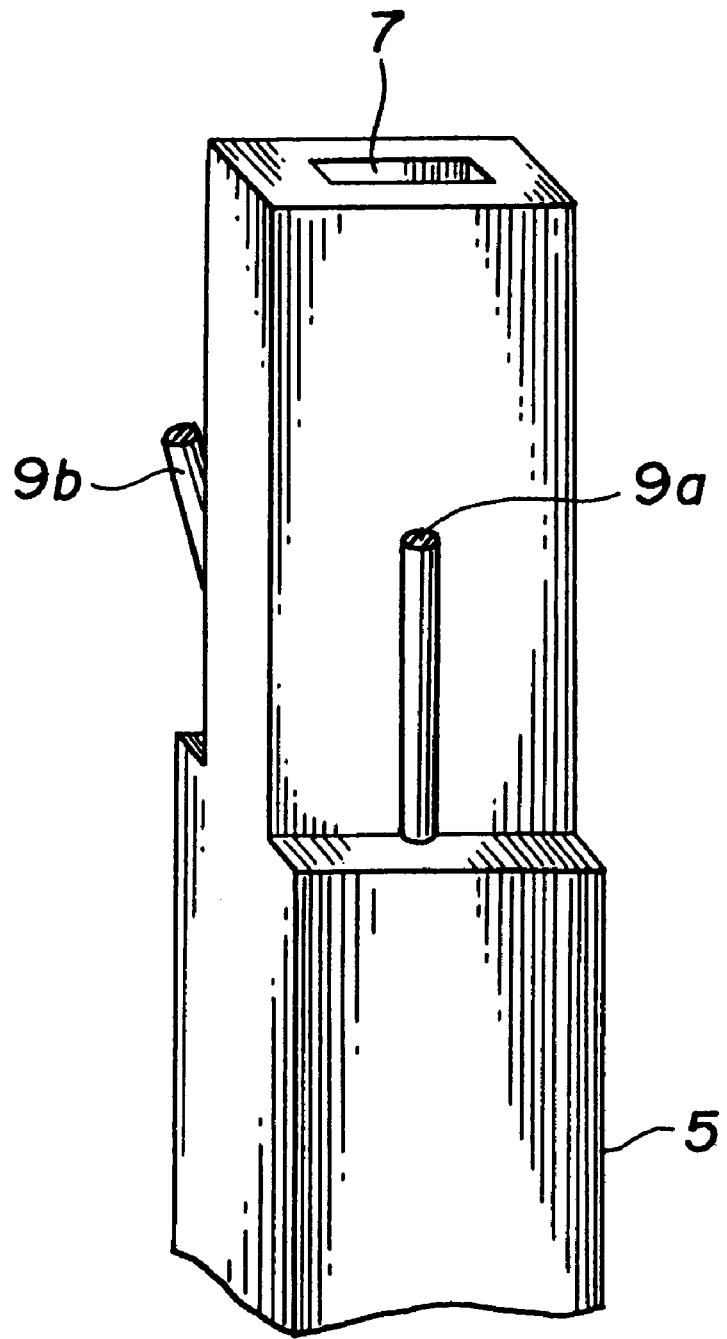

HEAT-RESISTING METAL-SHEATHED CABLE FOR SENSOR

BACKGROUND OF THE INVENTION

1. Field of the Invention

The present invention relates to a heat-resisting metal-sheathed cable for a sensor such as an oxygen sensor or thermistor which is disposed in a high temperature place in an automobile or the like.

2. Description of the Related Art

An oxygen concentration cell type oxygen sensor is heretofore known as a sensor for detecting an air-fuel ratio of an internal combustion engine such as an automotive engine. The oxygen sensor includes a pair of porous electrodes disposed on the opposite sides of a partition wall member made of an oxygen ion conductive solid electrolyte and is constructed so as to put one of the porous electrodes into contact with the reference gas and the other into contact with the measured gas (i.e., gas to be measured) such that the oxygen concentration is measured based on the electromotive force cell across the electrodes.

Accordingly, it is important that the reference gas is accurate. For example, if gasoline, water or the like into a chamber containing the reference gas, the reference gas is contaminated resulting in inaccurate detection. For this reason, it has heretofore been practiced to provide the chamber with an air-tight wall surrounding the reference gas thereby preventing ingress of contaminants into the chamber.

However, the above described technology still has a difficulty in preventing the ingress of contaminants completely, so it has been proposed to provide the chamber with an atmospheric air introducing hole which is devised to make it difficult for the contaminants to intrude therethrough into the chamber such that the chamber can be ventilated so as to contain the normal atmospheric air even if the contaminants intrude into the chamber a little.

For example, it is disclosed in Japanese utility model provisional publication No. 56-4852 such a technology of using a covered harness having an insulation covering made of a resinous material for fetching or output of signal, providing the harness with a hollow portion at the axial center thereof and using the hollow portion as a ventilation hole for passage or conduction of the atmospheric air.

However, since the recent oxygen sensors are generally used at a high temperature, such a harness having a resinous covering encounters a problem that it cannot withstand the heat at a high temperature.

Another technology describes a sensor provided with a filter for thereby attaining the permeability. However, this technology utilizes a filter made of a resinous material and thus encounters a problem that the sensor cannot be used at high temperatures.

As a countermeasure to such a problem, it is considered to use a stainless steel (SUS)-sheathed wire having a good resistance, for the above described harness. However, since a mass of magnesia power is used in the conventional SUS-sheathed wire as an insulator, it is difficult to form such a hollow portion as in the resinous harness, in the mass of magnesia powder. For this reason, the above described countermeasure encounters a problem that a desired ventilation hole cannot be formed in such a SUS-sheathed wire.

SUMMARY OF THE INVENTION

According to a first aspect of the present invention, there is provided a novel and improved heat-resisting metal-sheathed cable for a sensor, which comprises a sheathing tube made of heat-resisting metal, at least one conductor and at least one ventilation tube disposed at a predetermined interval within the sheathing tube, the ventilation tube being made of heat-resisting metal, and a mass of insulating powder filled in the sheathing tube in a way as to surround the conductor and the ventilation tube. Thus, the filling of the insulation powder within the sheathing tube makes it possible to attain a sufficient heat-resisting ability and a sufficient insulating ability, while making it possible to attain the ventilating ability by means of the ventilation tubes made of heat-resisting metal and disposed within the mass of insulating powder for the purpose maintaining the quality of the reference gas of the oxygen sensor.

According to a second aspect of the present invention, there is provided a heat-resisting metal-sheathed cable for a sensor, which comprises a sheathing tube made of heat-resisting metal, a pair of conductors and a pair of ventilation tubes disposed at predetermined intervals within the sheathing tube, the ventilation tube being made of heat-resisting metal, and a mass of insulating powder filled in the sheathing tube in a way as to surround the conductors and the ventilation tubes, wherein the conductors are respectively positioned at two of four corners of a square and the ventilation tubes are respectively positioned at remaining two of said four corners when observed in a cross sectional view of the sheathing tube. Though the inner diameter of the sheathing tube made of heat-resisting metal is generally so small, a short circuit between the conductors or the like fault never occurs since the pair of conductors and the pair of ventilation tubes are disposed so as to be positioned at four corners of a square, i.e., disposed so as to be distant from each other as much as possible according to the present invention.

According to a third aspect of the present invention, there is provided a cable as set forth in the second aspect, wherein the conductors and the ventilation tubes are disposed diagonally, respectively. By this, the conductors are disposed at diagonal positions, i.e., at positions most distant from each other, so a short circuit, or the like fault never occurs between the conductors. This is because the conductors are disposed so as to oppose diametrically each other, particularly when the ventilation tubes have a large diameter.

According to a fourth aspect of the present invention, there is provided a heat-resisting metal-sheathed cable for a sensor, which comprises a sheathing tube made for heat-resisting metal, a ventilation tube made of heat-resisting metal disposed concentrically within the sheathing tube, a plurality of conductors disposed at predetermined intervals within the sheathing tube and around the ventilation tube, and a mass of insulating powder filled in the sheathing tube in a way as to surround the conductors and the ventilation tube. The arrangement of disposing the ventilation tube concentrically within the sheathing tube enables the diameter of the ventilation tube to be set larger. Accordingly, sufficient ventilation can be attained even when a number of conductors are used in the cable.

According to a fifth aspect of the present invention, there is provided a cable according to the fourth aspect, wherein the conductors are respectively positioned at four corners of a square when observed in a cross sectional view of the sheathing tube. Though a short circuit is liable to be caused in case four conductors are used, this arrangement of disposing the conductors at positions distant from each other makes it possible to prevent a short circuit.

According to a sixth aspect of the present invention, there is provided a heat-resisting metal-sheathed cable for a sensor, which comprises an outer sheathing tube made of heat-resisting metal, an inner sheathing tube made of heat-resisting metal and disposed within the outer sheathing tube in a way as to provide between the two tubes a predetermined gap constituting a ventilation passage, at least one conductor disposed within the inner sheathing tube, and a mass of insulating powder filled in the inner sheathing tube in a way as to surround the conductor. By this, the space or passage for ventilation is shaped annular in cross section, so there is the advantage that the space can be made larger.

According to the seventh aspect of the present invention, there is provided a cable according to the sixth aspect, wherein the outer and inner sheathing tubes are secured to each other with welding. By this, the outer and inner sheathing tubes are assuredly held fixed or stationary to each other, thus making it possible to prevent the outer and inner sheathing tubes from striking against each other due to vibrations or the like and causing disconnection of the conductors or a short circuit between the conductors within the inner sheathing tube and therefore making it possible to improve the reliability of the cable.

According to an eighth aspect of the present invention there is provided a heat-resisting metal-sheathed cable for a sensor, which comprises a sheathing tube made of heat-resisting metal, at least one conductor disposed within the sheathing tube, and a mass of ceramic fibers disposed within the sheathing tube and surrounding the conductor. An example of such a mass or layer of ceramic fibers having a permeability is a ceramic yarn, and a number of pores and spaces between the ceramic fibers are used as a ventilation passage.

According to a further aspect of the present invention, there is provided a heat-resisting metal-sheathed cable for a sensor, which comprises a sheathing tube made of heat-resisting metal, a plurality of conductors disposed within the sheathing tube, a plurality of first masses of ceramic fibers disposed within the sheathing tube and surrounding the conductors to constitute insulated conductor assemblies, respectively, the insulated conductor assemblies being twisted into a bundle, and a second mass of ceramic fibers disposed within the sheathing tube and surrounding the bundle. Accordingly, even in the case a plurality of conductors are disposed within a sheathing tube, a short circuit never occurs between the conductors. Particularly, when the plurality of conductors covered by respective ceramic yarns are twisted into a bundle, the bundle has an outer surface having gentle undulations or irregularities. Thus, due to such undulations or irregularities, the bundle of conductor assemblies can be firmly held within the sheathing tube.

In the meantime, for the above described sheathing tubes and ventilation tubes, tubes made of stainless steel such as SUS310S, SUS304 or SUS316 according to Japanese Industrial Standards can be used. For the insulating powder, magnesia powder, alumina powder or the like can be used.

Further, the outer diameter of the sheathing tube can be within the range from 3.0 mm to 3.2 mm and the thickness can be within the range from 0.3 mm to 0.6 mm. The outer diameter of the ventilation tube can not be determined simply since it varies largely depending upon how the ventilation tube is disposed within the sheathing tube but such an outer diameter is desirable that allows for a ventilation passage having a cross sectional area ranging from 0.2 to 3 mm$^2$. The outer diameter of the conductors is desirable to be within the range from about 0.4 to 0.6 mm on consideration of the strength and the demand for the smaller diameter of the cable.

Further, for the ceramic fibers, fibers having heat resistance and insulation such as alumina fiber, silica fiber or alumina-silica fiber can be used. A ceramic yarn can be formed from ceramic fibers which are woven or twisted together. The diameter of the ceramic fibers forming such a ceramic yarn is desired to be within the range from 5 to 10 $\mu$m from the point of view of the easiness in weaving, the strength, etc.

The above structure is effective for solving the above noted problems inherent in the prior art cable for sensors that is used under a high temperature condition.

It is accordingly an object of the present invention to provide a novel and improved heat-resisting metal-sheathed cable for a sensor which has a good heat resistance and a ventilating ability or permeability for allowing oxygen or the like gaseous substance to pass therethrough.

It is a further object of the present invention to provide a novel and improved heat-resisting metal-sheathed cable of the foregoing character that is highly reliable in operation and particularly suited for use with an oxygen sensor or thermistor for automobiles.

It is a further object of the present invention to provide a novel and improved heat-resisting metal-sheathed cable of the foregoing character which is particularly useful and desirable from an air pollution preventing point of view.

BRIEF DESCRIPTION OF THE DRAWINGS

FIG. 2 is a fragmentary perspective view of a sensor element of the oxygen sensor of FIG. 1;

DETAILED DESCRIPTION OF THE PREFERRED EMBODIMENTS

A heat-resisting metal-sheathed cable for a sensor embodying the present invention will be described hereinafter with reference to the attached drawings.

(First Embodiment)

A heat-resisting metal-sheathed cable (hereinafter referred to simply as metal-sheathed cable) according to the first embodiment of the present invention is for use with one of oxygen sensors adapted for installation on an automotive vehicle exhaust pipe or manifold for instance, particularly an oxygen sensor of the type that requires a reference gas.

Figure 1:
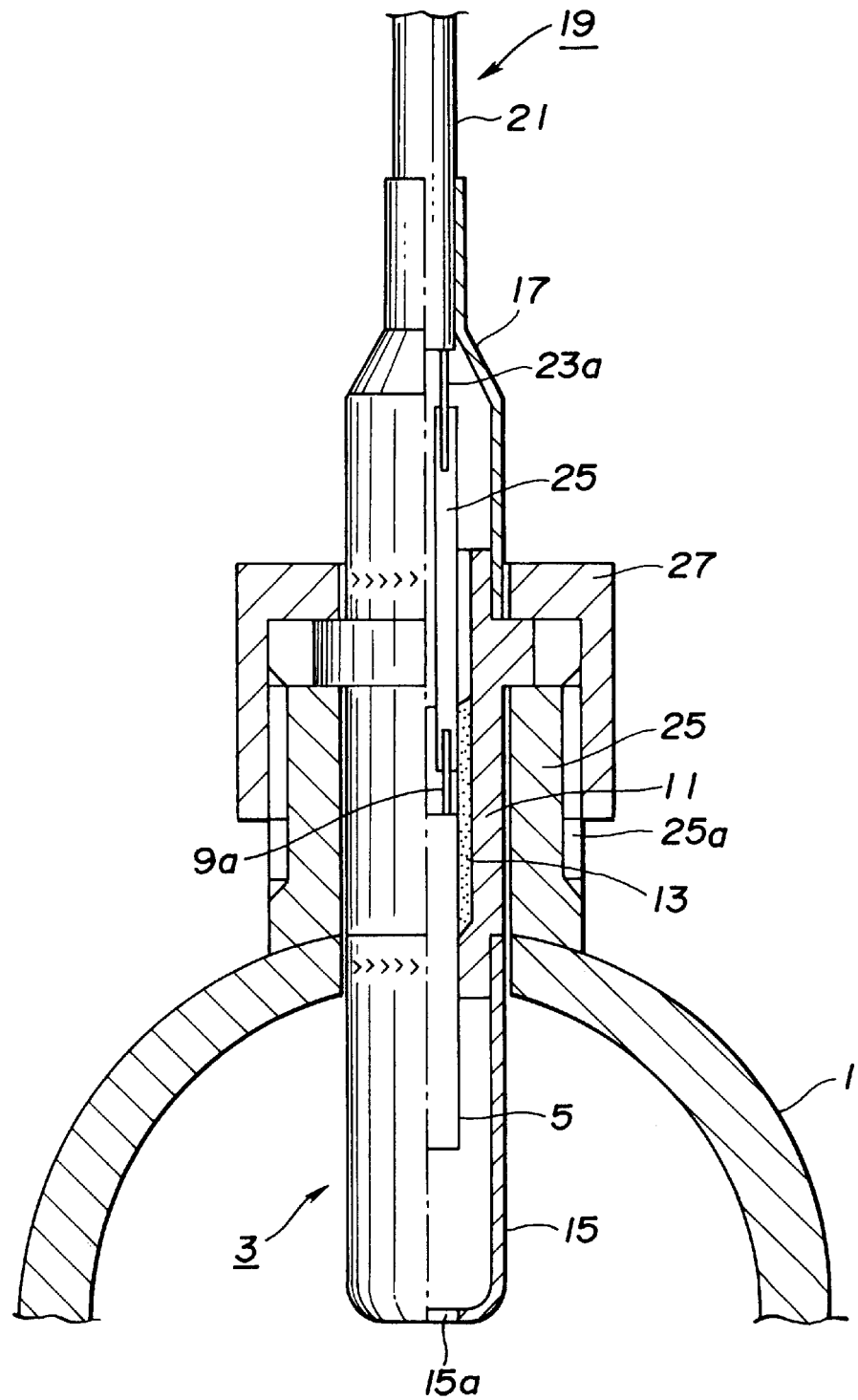
FIG. 1 is a fragmentary sectional view of an oxygen sensor installed on an exhaust pipe, together with a metal-sheathed cable in which the present invention is to be embodied.

(a) Referring first to FIGS. 1 and 2, an oxygen sensor with which the metal-sheathed cable embodying the present invention is used will be describe.

As shown in FIG. 1, installed on an exhaust pipe 1 is an oxygen sensor 3 that includes a sensor element 5 consisting of an oxygen ion conductive solid electrolytic partition wall member and a pair of porous electrodes disposed on the opposite sides of the partition wall member, i.e., a so-called oxygen concentration cell type oxygen sensor. The oxygen sensor 3 is constructed so as to subject one of the electrodes to the reference gas and the other electrodes to the measured gas (i.e., the gas to be measured) and detect the oxygen concentration in the measured gas based on the electromotive force cell across the electrodes.

The above described sensor element 5 has a reference oxygen chamber (not shown) into which a reference gas is introduced and has at a base portion thereof (i.e., at an upper portion thereof in the drawing), as shown in FIG. 2, an air hole 7 which is communicated with the reference oxygen chamber. Further, the sensor element 5 has at the base portion thereof a pair of electrode terminals 9a and 9b made of platinum (Pt) for outputting of the sensor.

Further, as shown in FIG. 1, the sensor element 5 is held fixed or secured within a tubular metal fixture 11 by means of glass seal or cement 13 in such a manner that an end portion of the sensor element 5 projects from an inner end of the fixture 11 into the exhaust pipe 1. To the inner end peripheral portion of the fixture 11 is fixed a metallic cover 15 having an opening 15a and covering the projected portion of the sensor element 5.

On the other hand, to an outer end portion of the metal fixture 11 is welded an end of a sleeve 17 made of stainless steel. The sleeve 17 is provided for the purpose of shutting off the inside of the metal fixture 11 from the outside while providing communication between the inside of the metal fixture 11 and the inside of a sheathing tube 21 of the metal-sheathed cable 19. The other end of the sleeve 17 is hermetically fixed or secured to the outer periphery of the sheathing tube 21 by welding or the like.

Within the inside of the sheathing tube 21 is disposed two conductors 23a and 23b (refer to FIG. 3) which are insulated from the sheathing tube 21. The two conductors 23a and 23b are electrically connected to the electrode terminals 9a and 9b disposed adjacent an outer end portion of the sensor element 5 by way of electrode leads 25, respectively.

The oxygen sensor 3 having the above described structure is fixed to the exhaust pipe 1 by being installed in an externally threaded tubular support 25 which is welded to the exhaust pipe 1 and then threadably engaging a cap nut 27 onto a threaded portion 25a of the support 25 to hold together the fixture 11.

(b) Description will be made as to how the metal-sheathed cable 19 is structured.

Figure 3A:
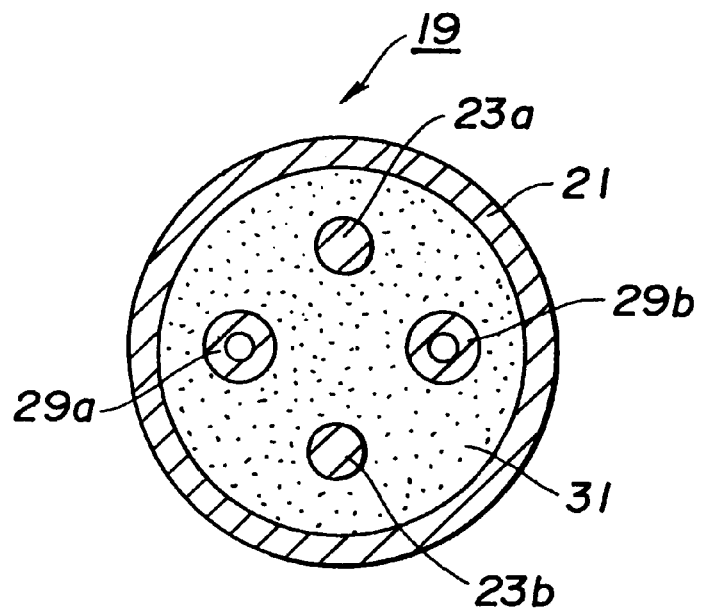
FIG. 3A is an elevational view of an end of a metal-sheathed cable according to the first embodiment of the present invention.
Figure 3B:
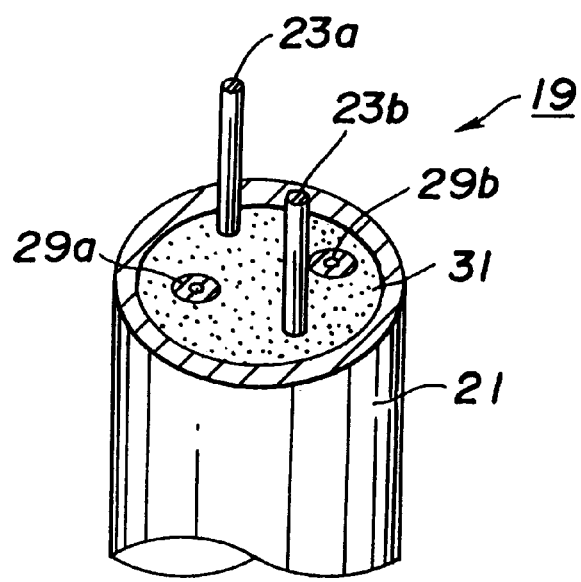
FIG. 3B is a perspective view of an end portion of the metal-sheathed cable of FIG. 3A.

As shown in FIGS. 3a and 3b, the metal-sheathed cable 19 includes a metallic pipe or tube (i.e., sheathing pipe or tube) 21 constituting an outer protective wall or covering of the cable 19, a pair of conductors 23a and 23b and a pair of metallic pipes or tubes (i.e., ventilation pipes or tube) 29a and 29b which are disposed within the metallic tube 21, and a mass 31 of insulating magnesia powder packed and compressed, i.e., filled in the metallic tube 21.

The above described sheathing tube 21 is made of stainless steel (SUS310S) and is 3.18 mm in diameter and 0.5 mm thick. The conductors 23a and 23b are made of nickel (Ni) and each consists of a single wire of 0.41 mm in diameter. The ventilation tubes 29a and 29b are made of stainless steel (SUS310S according to Japanese Industrial Standards) and are 0.53 mm in outer diameter and 0.2 mm in inner diameter.

The conductors 23a and 23b and the ventilation tubes 29a and 29b are disposed so as to be respectively positioned at four corners of a square when observed in a side elevation or cross sectional view of the cable 19 or tube 21. Accordingly, the sheathing tube 21, conductors 23a and 23b and ventilation tubes 29a and 29b are completely insulated from each other by the mass 31 of magnesia powder.

(c) The method of forming the metal-sheathed cable 19 will be described.

Firstly, magnesia powder is mixed with a binder and is extruded into a bar of a predetermined shape by an extruding machine for thereby forming a magnesia bar. More specifically, the extrusion is made so that the extruded magnesia bar is of the outer diameter ranging from 3.4 to 3.6 mm and has holes or openings through which the ventilation tubes 29a and 29b and the conductors 23a and 23b can pass, respectively.

The extruded magnesia bar is dried and provisionally sintered at the temperature ranging from 1000 to 1300° C.

Then, through the provisionally sintered magnesia bar are passed the conductors 23a and 23b and the ventilation tubes 29a and 29b, and the outer circumferential periphery of the magnesia bar is covered by the sheathing tube 21 of 3.8 mm in inner diameter and 4.6 mm in outer diameter.

Then, the sheathing tube 21 is cold drawn so as to reduce in diameter, i.e., so as to have the outer diameter ranging from 3.0 to 3.2 mm (in this embodiment, drawn so as to be 3.18 mm in outer diameter).

Thereafter, according to the necessity, the cold drawn product is annealed within a vacuum furnace at the temperature of 1050° C. to remove the stress of the sheathing tube 21 caused at the cold drawing, whereby to complete the metal-sheathed cable 19.

From the foregoing, it will be understood that the metal-sheathed cable 19 according to this embodiment is constructed so as to have the ventilation tubes 29a and 29b within the sheathing tube 19, so even in the case of the insulation structure using the mass 31 of insulating magnesia powder which is packed and compressed, i.e., filled in the sheathing tube 19 a ventilation passage for introducing a reference gas into the reference oxygen chamber of the oxygen sensor 3 by way of the ventilation hole 7 can be formed within the metal-sheathed cable 19 with ease and assuredness.

Further, the conductors 23a and 23b and the ventilation tubes 29a and 29b are disposed so as to be distant from each other as much as possible, so there results an advantage that a short circuit is hardly caused.

(Second Embodiment)

Description will now be made to the second embodiment in which similar portions to the first embodiment will be omitted for brevity or described briefly.

Figure 4A:
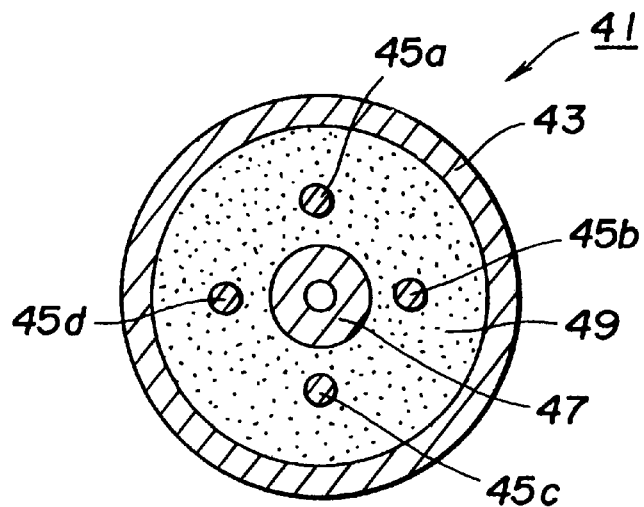
FIGS. 4A and 4B are views similar to FIGS. 3A and 3B, respectively but show the second embodiment.
Figure 4B:
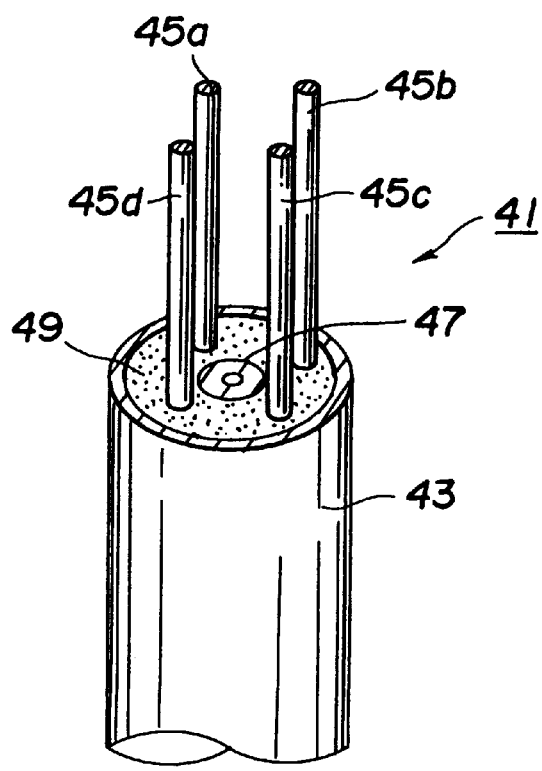

As shown in FIGS. 4A and 4B, a metal-sheathed cable 41 according the second embodiment includes a metallic sheathing tube 43 constituting an outer protective wall or covering of the cable 41, four conductors 45a to 45d and one metallic ventilation tube 47 disposed within the sheathing tube 43, and a mass 49 of insulating magnesia powder packed and compressed, i.e., filled in the sheathing tube 43.

Differing from the first embodiment, there are used in this embodiment four conductors, two of which are for fetching or taking out of the output of the sensor and the remaining two are connected to a heater (not shown) for heating the sensor element 5. Further, in the above described first embodiment, the ventilation tube can otherwise be constructed so as to double as a conductor.

The sheathing tube 43 is made of stainless steel (SUS304 according to Japanese Industrial Standards) and is 3.2 mm in outer diameter and 0.5 mm thick. The conductors 45a to 45d are made of nickel (Ni) and each consist of a single wire of 0.23 mm in outer diameter. The ventilation tube 47 is made of stainless steel (SUS304) and is 0.78 mm in outer diameter and 0.23 mm in inner diameter.

The ventilation tube 47 is disposed so as to be concentric with the sheathing tube 43, and the four conductors 45a to 45d are disposed around the ventilation tube 47 in such a way as to be positioned at four corners of a square when observed in an elevation or cross sectional view of the metal-sheathed cable 41.

Then, the method of producing the metal-sheathed cable 41 will be described briefly though basically similar to that described with respect to the first embodiment.

Firstly, magnesia powder is mixed with a binder and extruded into a bar of a predetermined size (8 cm in length) by an extruding machine to form a magnesia bar having holes or openings through which the ventilation tubes 47 and the conductors 45a to 45d can pass. In the meantime, the magnesia bar can be extended by being added with another magnesia bar for use in a longer sheathing tube, i.e., a longer cable.

Then, the extruded magnesia bar is provisionally sintered.

Through the provisionally sintered magnesia bar are passed the conductors 45a to 45d and the ventilation tube 47, and the outer circumferential periphery of the magnesia bar is covered by the sheathing tube 43.

Then, the sheathing tube 43 is cold drawn so as to reduce in diameter.

Thereafter, according to the necessity, the cold drawn product is annealed within a vacuum furnace, whereby to complete the metal-sheathed cable 41.

From the foregoing, it will be understood that the metal-sheathed cable 43 according to this embodiment is constructed so as to have the ventilation tube 47 at the center of or concentric with the sheathing tube 43 and the conductors 45a to 45d around the ventilation tube 47, so even in the case a number of conductors 45a to 45d are disposed within a limited space they can be distant from each other so as to make it possible to produce an advantage of a short circuit being hardly caused. Further, since the ventilation tube 47 is disposed at the center of or concentric with the sheathing tube 43, the ventilation tube 47 can be made larger in diameter considerably, thus making it possible to attain a better ventilation ability.

(Third Embodiment)

Description will be made to the third embodiment in which similar portions to the first embodiment is omitted for brevity or described briefly.

Figure 5A:
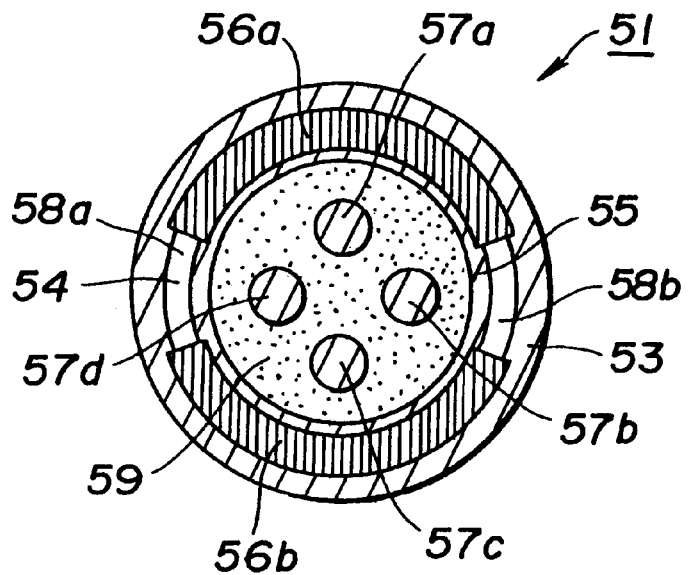
FIGS. 5A and 5B are views similar to FIGS. 3A and 3B, respectively but show the third embodiment.
Figure 5B:
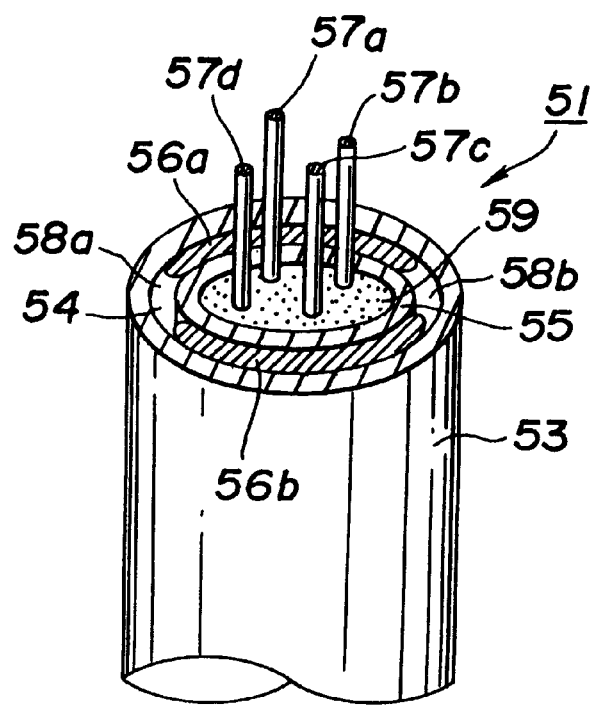

As shown in FIGS. 5A and 5B, a metal-sheathed cable 51 according to this embodiment includes an outer metallic sheathing tube 53 constituting an outer protective wall or covering of the cable 51, an inner metallic sheathing tube 55 constituting an inner protective wall of the cable 55 disposed within the sheathing tube 53, four conductors 57a to 57d disposed within the inner sheathing tube 53, and a mass 59 of insulating magnesia powder packed and compressed, i.e., filled in the inner sheathing tube 53 and around the conductors 57a to 57d.

Two of the four conductors are provided for fetching or taking out of the output of the sensor 3 and the remaining two are connected to the heater (not shown) for heating the sensor element 5.

The above described outer sheathing tube 53 is made of stainless steel (SUS316 according to Japanese Industrial Standards) and is 3.2 mm in outer diameter and 0.5 mm thick. The inner sheathing tube 55 is made of stainless steel (SUS316) and is 3.2 mm in outer diameter and 0.3 mm thick. The conductors 57a to 57d are made of nickel (Ni) and each consist of a single wire of 0.4 mm in diameter.

The outer sheathing tube 53 and the inner sheathing tube 55 are disposed concentric with each other while providing a small clearance or gap (about 0.35 mm) therebetween and welded together at end portions (i.e., the hatched portions in FIG. 5A) 56a and 56b in such a manner that the above described clearance or gap is retained. By this, an annular passage 54 having open end portions 58a and 58b disposed on horizontally opposed sides in FIG. 5A. Further, the conductors 57a to 57d are disposed within the inner sheathing tube 55 in such a way as to be respectively positioned at four corners of a square when observed in an elevation or cross sectional view of the cable 51.

The method of producing the metal-sheathed cable 51 will be described briefly though partially similar to that described with respect to the first embodiment.

Firstly, magnesia powder is mixed with a binder and extruded into a bar of a predetermined size by an extruding machine to form a magnesia bar having holes or openings through which the conductors 57a to 57d can pass.

Then, the extruded magnesia bar is dried and provisionally sintered.

Through the provisionally sintered magnesia bar are passed the conductors 57a to 57d, and the outer circumferential periphery of the magnesia bar is covered by the inner sheathing tube 55.

Then, the inner sheathing tube 55 is cold drawn so as to reduce in diameter.

Thereafter, according to the necessity, the cold drawn product is annealed within a vacuum furnace.

The inner sheathing tube 55 is disposed within the outer sheathing tube 53 and held stationary relative to same in a way as to provide a predetermined annular clearance or gap therebetween by means of a jig or the like. Under such a condition of the inner sheathing tube 55 being held stationary relative to the outer sheathing tube 53, portions of each end of the inner sheathing tube 55 are welded to corresponding portion of each end of the sheathing tube 53, whereby to complete the metal-sheathed cable 51.

From the foregoing, it will be understood that the metal-sheathed cable 51 of this embodiment has the inner sheathing tube 55 which is disposed within the outer sheathing tube 53 in such a manner as to form the ventilation passage 54 of an annular cross section, so even in the case of the insulation structure using the mass 59 of insulating magnesia which is packed and compressed, i.e., filled in the inner sheathing tube 55 a ventilation passage for introducing a reference gas into the reference oxygen chamber of the oxygen sensor 3 can be formed within the metal-sheathed cable 51 with ease and assuredness.

Particularly, by this embodiment, an annular cross sectional passage 54 having a large cross sectional area can be formed between the inner and outer sheathing tubes 55 and 53, thus making it possible to introduce the reference gas more easily.

(Fourth Embodiment)

Description will be made to the fourth embodiment in which similar portions to the first embodiment will be omitted for brevity or described briefly.

Figure 6A:
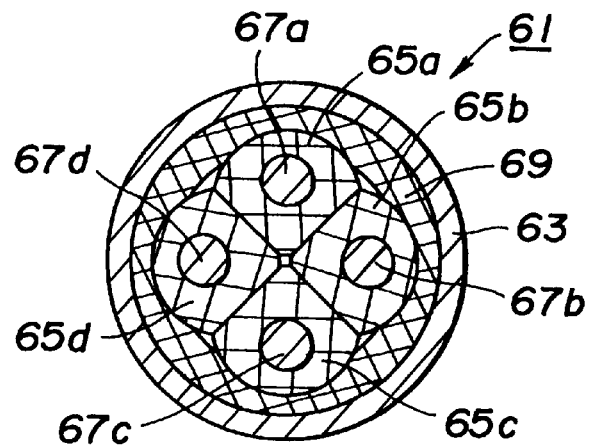
FIGS. 6A and 6B are vies similar to FIGS. 3A and 3B, respectively but show the fourth embodiment.
Figure 6B:
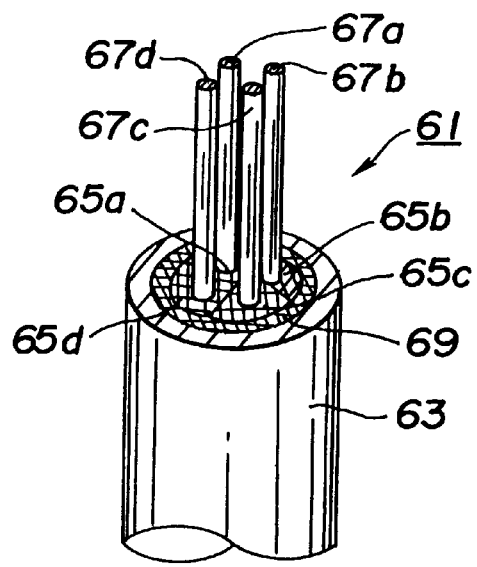
Figure 6C:
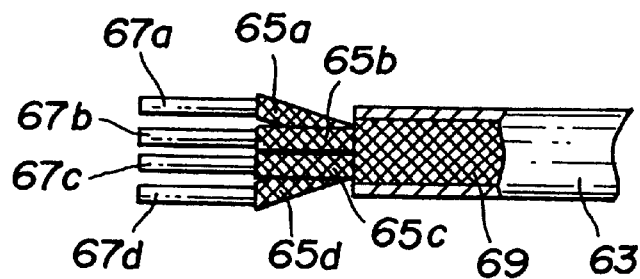
FIG. 6C is an illustration of how conductors of the cable of FIGS. 6A and 6B are twisted.

As shown in FIGS. 6A to 6C, the metal-sheathed cable 61 of this embodiment includes a metallic sheathing tube 63 constituting an outer protective wall or covering of the cable 61, four conductors 67a to 67d disposed within the sheathing tube 63, first masses of ceramic fibers or first ceramic yarns 65a to 65d covering or surrounding the conductors 67a to 67d, respectively and a second mass of ceramic fibers or second ceramic yarn 69 covering or surrounding the first ceramic yarns 65a to 65d.

Two of the four conductors are for outputting of the sensor 3, and the remaining two of the conductors are connected to the heater (not shown) for heating the sensor element 5.

The sheathing tube 63 is made of stainless steel (SUS310S according to the Japanese Industrial Standards) and is 3.2 mm in outer diameter and 0.5 mm thick. The conductors 67a to 67d are made of nickel (Ni) and each consist of a single wire of 0.45 mm in diameter.

The first ceramic yarns 65a to 65d are tubular fibrous bodies formed from woven ceramic fibers (e.g., alumina fiber of 7 $\mu$m thick), so the conductors 67a to 67d are covered by the fibrous bodies to constitute assemblies of conductors 67a to 67d and ceramic yarns 65a to 65d, i.e., insulated conductor assemblies. As seen from FIG. 6C, the four insulated conductor assemblies are twisted into a bundle having an irregular or rugged outer surface, and the outer periphery of the bundle is covered by the second ceramic yarn 69 which is a tubular fibrous body formed similarly to the first ceramic yarns 65a to 65d. In the meantime, in FIGS. 6A to 6C, the first ceramic yarns 65a to 65d and the second ceramic yarn 69 of ceramic are shown by crosshatching.

Then, the method of producing the metal-sheathed cable 61 will be described briefly.

Firstly, around the conductors 67a to 67d made of nickel (Ni) are respectively formed the ceramic yarns 65a to 65d by weaving of a long-fiber of alumina of 7 $\mu$m thick for thereby forming the above described insulated conductor assemblies.

Then, as shown in FIG. 6C, the insulated conductor assemblies are twisted into a bundle, and around the bundle is formed the second ceramic yarn 69 by weaving of a long-fiber of alumina for thereby forming an insulated bundle of conductors.

The insulated bundle of conductors are disposed within the sheathing tube 63 of 4.0 mm in diameter and 0.4 mm thick and processed by a rotary swaging machine in such a manner that the outer diameter of the assembly is reduced to 3.2 mm, whereby to complete the metal-sheathed cable 61.

From the foregoing, it will be understood that the metal-sheathed cable 61 of this embodiment has within the sheathing tube 63 the conductors 65a to 65d which are covered by the first ceramic yarns 67a to 67d and the second ceramic yarn 69, so the conductors 65a to 65d can be held insulated from each other and from the sheathing tube 63, while a ventilation passage for introduction or conduction of the reference gas into the reference oxygen chamber of the oxygen sensor can be formed with ease within the metal-sheathed cable by utilizing the space between the fibers of the first ceramic yarns 65a to 65d and the second ceramic yarn 69.

Particularly, in this embodiment, the four conductors 67a to 67d are twisted into a bundle having an irregular or rugged outer surface, so by the effect of such an irregular or rugged surface it becomes possible to prevent the bundle of the conductors 67a to 67d from moving out of place within the sheathing tube 63 or being removed from the sheathing tube 63.

While the present invention has been described and shown as above, it is not for the purpose of limitation but various variations or modifications thereof can be made within the scope of the appended claims.

What is claimed is:

1. A heat-resisting metal-sheathed cable for a sensor, comprising:

an outer sheathing tube made of heat-resisting metal;

an inner sheathing tube made of heat-resisting metal and disposed within said outer sheathing tube with a predetermined gap between an inner circumferential surface of said outer sheathing tube and an outer circumferential surface of said inner sheathing tube;

ventilation passage means for conducting ventilation fluid therethrough;

said ventilation passage means including a ventilation passage which is constituted by said predetermined gap;

at least one conductor disposed within said inner sheathing tube; and a mass of insulating powder disposed within said inner sheathing tube and around said at least one conductor.

2. A cable according to claim 1, wherein said outer and inner sheathing tubes are secured to each other with welding.

3. A combination comprising:

an oxygen sensor including at least one output terminal and a reference gas passage; and a heat-resisting metal-sheathed cable including an outer sheathing tube made of heat-resisting metal, an inner sheathing tube made of heat-resisting metal and disposed within said outer sheathing tube with a predetermined gap between an inner circumferential surface of said outer sheathing tube and an outer circumferential surface of said inner sheathing tube, ventilation passage means for conducting ventilation fluid therethrough, said ventilation passage means including a ventilation passage which is constituted by said predetermined gap, at least one conductor disposed within said inner sheathing tube, said ventilation passage being fluidly connected to said reference gas passage of said oxygen sensor, said at least one conductor being electrically connected to said at least one output terminal of said oxygen sensor, and a mass of insulating powder disposed within said inner sheathing tube and around said at least one conductor.

4. A heat-resisting metal-sheathed cable for a sensor, comprising:

an outer sheathing tube made of heat-resisting metal;

an inner sheathing tube made of heat-resisting metal and disposed within said outer sheathing tube with a predetermined gap comprising an open ventilation passage between an inner circumferential surface of said outer sheathing tube and an outer circumferential surface of said inner sheathing tube;

at least one conductor disposed within said inner sheathing tube; and a mass of insulating powder disposed within said inner sheathing tube and around said at least one conductor.

* * * * *